US008835166B2

(12) United States Patent
Phillips et al.

(10) Patent No.: US 8,835,166 B2
(45) Date of Patent: Sep. 16, 2014

(54) EXTRACELLULAR MATRIX MATERIAL CREATED USING NON-THERMAL IRREVERSIBLE ELECTROPORATION

(75) Inventors: Mary Phillips, Berkeley, CA (US); Elad Maor, Berkeley, CA (US); Boris Rubinsky, El Cerrito, CA (US); Jacob Lavee, Ramat Gan (IL)

(73) Assignee: The Regents of the University of California, Oakland, CA (US)

( * ) Notice: Subject to any disclaimer, the term of this patent is extended or adjusted under 35 U.S.C. 154(b) by 28 days.

(21) Appl. No.: 13/391,577

(22) PCT Filed: Sep. 2, 2010

(86) PCT No.: PCT/US2010/047725
§ 371 (c)(1),
(2), (4) Date: Apr. 27, 2012

(87) PCT Pub. No.: WO2011/028937
PCT Pub. Date: Mar. 10, 2011

(65) Prior Publication Data
US 2012/0226218 A1    Sep. 6, 2012

Related U.S. Application Data

(60) Provisional application No. 61/239,923, filed on Sep. 4, 2009.

(51) Int. Cl.
| | |
|---|---|
| *A61B 18/18* | (2006.01) |
| *A61L 2/03* | (2006.01) |
| *A61L 27/38* | (2006.01) |
| *A61K 35/44* | (2006.01) |
| *A61K 35/38* | (2006.01) |
| *A61K 35/42* | (2006.01) |
| *A61K 35/22* | (2006.01) |
| *A61K 35/34* | (2006.01) |
| *A61L 27/36* | (2006.01) |

(52) U.S. Cl.
CPC .............. *A61K 35/34* (2013.01); *A61L 27/3834* (2013.01); *A61K 35/44* (2013.01); *A61K 35/38* (2013.01); *A61L 2430/40* (2013.01); *A61K 35/42* (2013.01); *A61K 35/22* (2013.01); *A61L 27/3683* (2013.01); *A61L 27/3604* (2013.01)
USPC ............................................ 435/325; 607/50

(58) Field of Classification Search
CPC ... A61K 6/00; A61K 41/00; A61K 2201/032; A61K 35/34; A61K 35/44; A61L 2430/00; A61L 2430/30; A61L 2430/40; A61L 27/3604; A61L 27/3683; A61B 18/00; A61B 18/12; A61B 2018/00; A61B 2018/00071; A61B 2018/00315; A61B 2018/00613
See application file for complete search history.

(56) References Cited

U.S. PATENT DOCUMENTS

| 2004/0176855 A1* | 9/2004 | Badylak ...................... 623/23.72 |
| 2009/0269317 A1* | 10/2009 | Davalos ....................... 424/93.7 |

FOREIGN PATENT DOCUMENTS

WO    WO 0103750 A1 *  1/2001

OTHER PUBLICATIONS

Badylak, S. et al. 2003. Extracellular Matrix for Myocardial Repair. The Heart Surgery Forum 6(2):E20-E26. specif. p. E20.*
Maor, E. et al. 2007. The Effect of Irreversible Electroporation on Blood Vessels. Technology in Cancer Research and Treatment (6)4:307-312. specif. p. 308.*
Davalos, R.V. et al. 2005. Tissue Ablation with Irreversible Electroporation. Annals of Biomedical Engineering 33(2):223-231. specif. p. 223.*
Maurer, B. et al. 2006. Autologous haematopoietic stem cell transplantation for Behcet's disease with pulmonary involvement: analysis after 5 years of follow up. Annals of the Rheumatic Diseases 65:127-129. specif. p. 127.*
Phillips et al., "Nonthermal Irreversible Electroporation for Tissue Decellularization" Journal of Biomechanical Engineering, 132:091003-1-091003-8 (Sep. 2010).
Phillips et al., "Principles of Tissue Engineering With Nonthermal Irreversible Electroporation" Journal of Heat Transfer, 133:011004-1-011004-8 (Jan. 2011).
Ott et al., "Perfusion-decellularized matrix: using nature's platform to engineer a bioartifical heart" Nature Medicine, Advanced Online Publication, pp. 1-9 (Jan. 13, 2008).

* cited by examiner

*Primary Examiner* — John S Brusca
*Assistant Examiner* — Sharon M Papciak
(74) *Attorney, Agent, or Firm* — Karl Bozicevic; Bozicevic, Field & Francis LLP

(57) ABSTRACT

Extracellular matrix material is disclosed which is created by subjecting a target area to non-thermal irreversible electroporation (NTIRE) with a pulsed electrical field to kill cells in the absence of thermal damage. The dead cellular material may be removed and the remaining non-cellular matrix material may be implanted into a repair site to be treated medically or cosmetically.

1 Claim, 2 Drawing Sheets

EXTRACELLULAR MATRIX MATERIAL CREATED USING NON-THERMAL IRREVERSIBLE ELECTROPORATION

CROSS REFERENCES

This application is a 371 National Stage Application of International Patent Application Serial No. PCT/US2010/047725, filed Sep. 2, 2010, which application claims to benefit of priority to U.S. Provisional Application Ser. No. 61/239,923, filed Sep. 4, 2009, both of which are incorporated herein by reference in their entirety noting that the current application controls to the extent there is any contradiction with any earlier applications and to which applications we claim priority under 35 USC §120.

FIELD OF THE INVENTION

This invention relates generally to extracellular matrix material and more particularly to the use of a particular process in the form of non-thermal irreversible electroporation in order to create extracellular matrix material which can be used as an implant.

BACKGROUND OF THE INVENTION

It is known to use naturally occurring extracelluar matrices (ECMs) to provide a scaffold for tissue repair and regeneration. One such ECM is small intestine submucosa (SIS). SIS has been described as a natural biomaterial used to repair, support, and stabilize a wide variety of anatomical defects and traumatic injuries. The SIS material is derived from porcine small intestinal submucosa that models the qualities of its host when implanted in human soft tissues. Further, it is taught that the SIS material provides a natural matrix with a three-dimensional structure and biochemical composition that attracts host cells and supports tissue remodeling. SIS products, such as OASIS™ and SURGISIS™, are commercially available from Cook Biotech Inc., Bloomington, Ind.

Another SIS product, RESTORE® Orthobiologic Implant, is available from DePuy Orthopaedics, Inc. in Warsaw, Ind. The DePuy product is described for use during rotator cuff surgery, and is provided as a resorbable framework that allows the rotator cuff tendon to regenerate. The RESTORE Implant is derived from porcine small intestine submucosa, a naturally occurring ECM composed primarily of collagenous proteins, that has been cleaned, disinfected, and sterilized. Other biological molecules, such as growth factors, glycosaminoglycans, etc., have also been identified in SIS. See: Hodde et al., Tissue Eng., 2(3): 209 217 (1996); Voytik-Harbin et al., J. Cell. Biochem., 67: 478 491 (1997); McPherson and Badylak, Tissue Eng., 4(1): 75 83 (1998); Hodde et al., Endothelium 8(1): 11 24; Hodde and Hiles, Wounds, 13(5): 195 201 (2001); Hurst and Bonner, J. Biomater. Sci. Polym. Ed., 12(11): 1267 1279 (2001); Hodde et al., Biomaterial, 23(8): 1841 1848 (2002); and Hodde, Tissue Eng., 8(2): 295 308 (2002). During seven years of preclinical testing in animals, there were no incidences of infection transmission from the implant to the host, and the SIS material has not adversely affected the systemic activity of the immune system. See: Allman et al., Transplant, 17(11): 1631 1640 (2001); Allman et al., Tissue Eng., 8(1):53 62 (2002).

While small intestine submucosa is available, other sources of ECM are known to be effective for tissue remodeling. These sources include, but are not limited to, stomach, bladder, alimentary, respiratory, and genital submucosa. In addition, liver basement membrane is known to be effective for tissue remodeling. See, e.g., U.S. Pat. Nos. 6,379,710, 6,171,344, 6,099,567, and 5,554,389, hereby incorporated by reference. Further, while ECM is most often porcine derived, it is known that these various ECM materials can be derived from non-porcine sources, including bovine and ovine sources. Additionally, the ECM material may also include partial layers of laminar muscularis mucosa, muscularis mucosa, lamina propria, stratum compactum layer and/or other such tissue materials depending upon other factors such as the source from which the ECM material was derived and the delamination procedure.

The following patents, hereby incorporated by reference, disclose the use of ECMs for the regeneration and repair of various tissues: U.S. Pat. Nos. 6,379,710; 6,187,039; 6,176,880; 6,126,686; 6,099,567; 6,096,347; 5,997,575; 5,993,844; 5,968,096; 5,955,110; 5,922,028; 5,885,619; 5,788,625; 5,733,337; 5,762,966; 5,755,791; 5,753,267; 5,711,969; 5,645,860; 5,641,518; 5,554,389; 5,516,533; 5,460,962; 5,445,833; 5,372,821; 5,352,463; 5,281,422; and 5,275,826.

Tissue engineering attempts to replace diseased tissues of the body with engineered replacements. One of the most important applications of tissue engineering is for treatment of cardiovascular diseases. Clinical treatment of disease and trauma to the coronary arteries and the peripheral vessels often includes the use of bypass grafting. In 2006, approximately 448,000 cardiac revascularizations were performed in the United States alone.

The choice of the graft is critically important and plays a major role in the success of the procedure. Autologous grafts are most often used, and are typically taken from the saphenous vein, internal mammary artery, or the radial artery[2]. This method, however, is not always an option since many patients do not have a vein that is suitable to use. Also, the costs associated with harvesting autologous vessels are considerable, and there is a significant level of morbidity associated with the procedure[3].

Synthetic grafts such as Dacron or polytetrafluoroethylene have also been used with some success. When it comes to the treatment of small diameter vessels, however, the use of these grafts tends to lead to poor compliance and low patency, often resulting in thrombogenicity due to lack of endothelial cells and anatomic intimal hyperplasia[4]. Thus, an alternative graft is sought that can meet the disadvantages and shortcomings seen in both autologous and synthetic grafts.

Recently, tissue engineering has been looked at as a promising solution to the issues at hand. Such methods often include developing a scaffold that is seeded with cells in vitro or implanted and allowed to repopulate in vivo. By decellularizing either xenographic or human based tissue and repopulating it with the recipient's own cells, a scaffold can be derived that, in theory, eliminates the need for immunesuppressant drugs and reduces the risk of graft rejection. Such a scaffold consists of an extracellular matrix (ECM) that is not only rich in cell signaling components essential for cell adhesion, migration, proliferation, and differentiation, but also has a greater resistance to infection than synthetic materials[5].

Recent research has focused on a variety of tissue decellularization methods. Many different protocols have been tested that typically include some combination of physical, chemical, and/or enzymatic processes[3,6,7,8]. Though the results from such work have shown promise, there has been little long term follow-up[2]. These methods also risk damage to the ECM, possibly compromising the scaffold's further development and integration into the recipient's body[9]. For example, chemicals used in the treatment process may not be completely removed after use. These chemicals could prove toxic to the host cells[9] and result in long term stenosis in vivo due to insufficient cell ingrowth[7]. Also, some chemical treatments used such as acids, non-ionic detergents, and ionic detergents may remove important molecules such as GAGs from collagenous tissues, resulting in slowed cell migration and a reduced chance for the tissue to properly remodel in vivo[9]. Enzymes used to decellularize the tissue such as DNase, RNase, and trypsin could also pose a problem, invoking an adverse immune response by the host[9]. Physical techniques are also not without potential risk, and methods such as snap freezing and mechanical agitation can disrupt the ECM as the cellular material is removed[9]. Some of these issues, such as insufficient cell ingrowth in vivo, can be addressed by seeding the scaffolds in vitro prior to implantation. These techniques, however, require time (typically at least 8 weeks), local expertise, and bioreactor facilities[5], making them both costly and impractical for emergency procedures.

SUMMARY OF THE INVENTION

The invention includes a method of treatment comprising subjecting a target area of tissue in a mammal to non-thermal irreversible electroporation (NTIRE) in order to kill cells at the target site. The NTIRE may kill substantially all or all of the cells at the target site and may do so without the use of any chemical agents, toxins, enzymes or use of physical devices beyond the NTIRE devices. After the application of the NTIRE the area of target tissue may be left in place for a period of time which can vary with the site and/or the patient in order to allow the immune system of the patient to remove cells which have been killed with the NTIRE. The period of time may be 1, 2, 3, 4 days or more. After the immune system has removed cells killed with the NTIRE, and before there is substantial growth (or any detectable growth) of new cells the tissue is removed from the mammal and transplanted to a repair site. The repair site may be in the same patient and as such be autografting. The repair site may be in a different animal which animal is of the same species, and thus constitute allografting or may be in an animal of a different species and constitute xenografting and may be carried out in the absence of any immunosuppressant drugs.

The patient may be a human and the tissue may be any type of tissue for example the tissue may be of blood vessels such as a portion of an artery or an intestine such as a portion of the small intestine.

The process can carry out the cell removal in the absence of any chemicals, toxins or enzymes which might generally be used to in order to eliminate the cells. The transplantation may be used in the absence of any immune-suppressant drugs with a reduced risk of graph rejection. The extracellular matrix produced by the invention is rich in cell signaling components essential for cell adhesion, migration, proliferation and differentiation. Further, the extracellular matrix produced by the invention has a greater resistance to infection as compared to synthetic materials.

Another aspect of the invention is the extracellular matrix produced by the process of the invention which matrix may be seeded with stem cells (e.g. human embryonic stem cells (hESCs) or adult stem cells) and used for any purpose including cosmetic surgery.

Yet another aspect of the invention is a use of the non-thermal irreversible electroporation in manufacturing an extracellular matrix for treatment of various types include treatment of damaged tissue and for tissue repair and augmentation.

Another aspect of the invention is the use of tissue in manufacturing an extracellular matrix for repair of a body part, wherein the tissue is subjected to non-thermal irreversible electroporation in order to kill cells in the tissue. The resulting matrix produced may be stored in a container and sealed away from outside pathogens for future use.

An aspect of the invention is a decellularized tissue produced by subjecting an area of tissue to non-thermal irreversible electroporation (NTIRE) and removing that tissue from a donor animal and implanting that tissue into a recipient animal where the donor and recipient may be of a different species (pig to human) or the same species or even the same animal.

Another aspect of the invention is carrying out tissue repair such as on a vessel by implanting the decellularization tissue described here.

Another aspect of the invention is to carry out the NTIRE in a method without the use of any chemical, toxin or enzymes or physical steps generally used for decellularization.

An aspect of the invention is an extracellular matrix (which may be seeded with live human pluripotent cells) for use as a medicament for tissue repair which includes cosmetic repair of tissue.

These and other objects, advantages, and features of the invention will become apparent to those persons skilled in the art upon reading the details of the methods and materials as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION OF THE INVENTION

Figure 1:
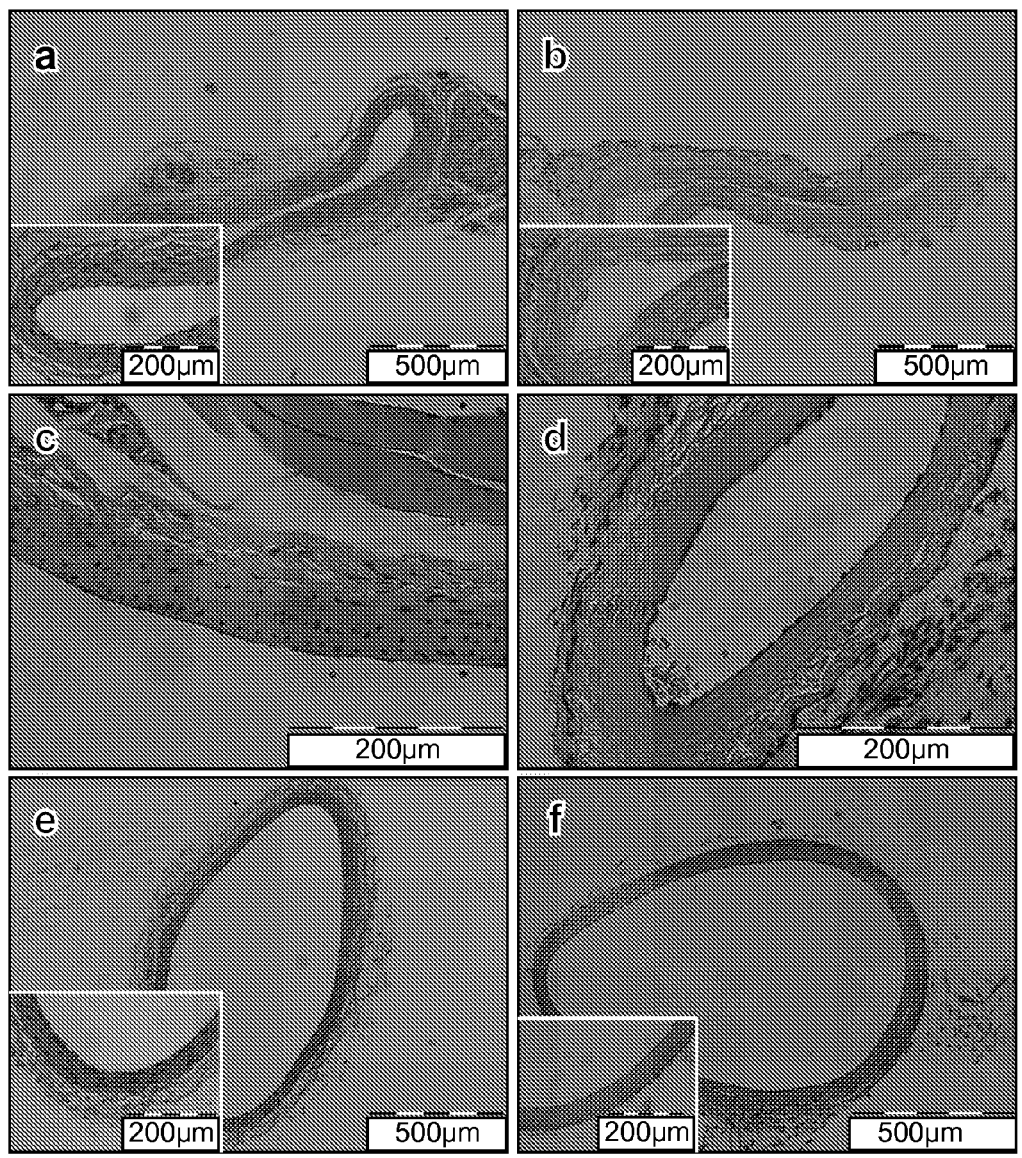
FIG. 1. Effect of NTIRE on blood vessels. NTIRE-treated arteries (right column) are compared to the controls (left column). H&E staining at three days post treatment (a) shows a marked decrease in VSMC when compared with the control (b). Results for the 5-day group are shown in (c) and (d), and the 7-day group is shown in (e) and (f). Note the repopulation of endothelial cells at five and seven days as seen in (d) and (f), respectively.

Before the present methods and materials are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein and the prior provisional application 61/239,923 are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a tissue sample" includes a plurality of such tissue samples and reference to "the pulse" includes reference to one or more pulses and equivalents thereof known to those skilled in the art, and so forth.

The publications discussed herein are provided solely for their disclosure prior to the filing date of the present application and are incorporated herein by reference. Nothing herein is to be construed as an admission that the present invention is not entitled to antedate such publication by virtue of prior invention. Further, the dates of publication provided may be different from the actual publication dates which may need to be independently confirmed.

DEFINITIONS

The terms "extracellular material" and "extracellular matrix" and the like refer to tissue which has been subjected to a process that kills any living cells. The process used here is NTIRE. The tissue may include areas which include no cells along with areas that have cells and the NTIRE may be focused only on the areas comprised of cells to create "extracellular material." The tissue may be treated by NTIRE in a fashion so that after treatment it maintains characteristic such as structural integrity that allow the tissue to be useful when transplanted to a repair site.

The terms "autografting" and "autograft" and the like refer to material taken from a patient such as a human and transplanted elsewhere within the same patient.

The terms "allografting" and "allograft" and the like are referred to removing tissue from a patient of a given species such as a human and transplanting that tissue into another patient of the same species such as another human.

The terms "xenographic material", "xenographic tissue" and the like refer to tissue from one animal species (e.g., porcine) transplanted to a different animal species (e.g. *Homo sapiens*).

INVENTION IN GENERAL

Tissue scaffolds in the form of an extracellular matrix (ECM) are produced by decellularization of living tissue using non-thermal irreversible electroporation (NTIRE) which are pulsed electrical fields that result in creating nanoscale irreversible damage to the cell membrane in the targeted tissue while maintaining the structural integrity of the ECM. Thereafter the immune response of the host body is utilized in order to remove proteins and cellular materials. The scaffold can be used to facilitate tissue repair which can be any type of tissue repair including cosmetic tissue repair.

In one embodiment a two-dimensional transient finite element solution of the Laplatce and heat conduction equations can be used to ensure that the electrical parameters used do not result in thermal damage to the tissue scaffold. By performing NTIRE in vivo on the carotid artery waiting three days after the NTIRE the immune system decellularizes the irreversibly electroporated tissue and leaves behind a functional scaffold. If the tissue is left in place for seven days endothelial regrowth occurs indicating that the artery scaffold maintains its function throughout the procedure that normal recellularization will take place.

An extracellular matrix for use in a treatment is disclosed. The matrix is produced by a process comprising the steps of first subjecting a target area of tissue in a mammal to nonthermal irreversible electroporation (NTIRE) in order to kill cells in the target area. Second, the mammals immune system is allowed to remove cells killed by the NTIRE which means leaving the targeted tissue in place in the mammal for three days plus or minus one day. Lastly, the targeted area of tissue is removed from the mammal thereby providing the extracellular matrix with the cellular material and proteins removed. The extracted matrix or scaffold is isolated away from the mammal and may be seeded with live cells (e.g. stem cells such as adult stem cells or embryonic stem cells) which may be from the recipient animal which will receive the extracellular matrix for tissue repair.

The tissue which is targeted and used for tissue repair may be used for any type of tissue including but not limited to parts of or entire organs such as blood vessels, a heart, a lung, an intestine which may be a small intestine or a large intestine or a bladder.

One aspect of the invention is a method of treatment which may be a method of cosmetic treatment or a method of curing a patient with respect to tissue damage. The method comprises subjecting a target area of tissue in the mammal to NTIRE in order to kill cells and then allowing the mammal's immune system or other systems in the mammal to remove cellular material including proteins which might cause an immune response when transplanted to a different animal. Thereafter the extracellular matrix or tissue scaffold is removed or transplanted to a repair site in the same animal, or a different animal of the same species or a different animal of a different species. Because the process allows for the removal of cellular materials and proteins by the immune system the transplantation can be carried out in the absence of any immunosuppressive drugs.

Another aspect of the invention is use of non-thermal irreversible electroporation (NTIRE) in manufacturing an extracellular matrix for treating tissue damage including in a cosmetic surgery.

Another aspect of the invention is use of a tissue in manufacturing an extracellular matrix for repair of a body part, wherein tissue is subjected to nonthermal irreversible electroporation (NTIRE) to kill cells in the tissue.

Another aspect of the invention is an extracellular matrix for use as a medicament which extracellular matrix is produced by the process as described here.

Another aspect of the invention is the use of the extracellular matrix (which may be seeded with stem cells such as hESCs) for the manufacture of a medicament for the treatment of tissue repair which may be a specific type of tissue repair as described herein including cosmetic tissue repair.

Another aspect of the invention is the extracellular matrix for use in a treatment of specific disease such as treating blocked arteries by bypass surgery and removing blocked portions and grafting in an extracellular matrix of the invention which is a vessel from the same animal, a different animal of the same species or a different animal of a different species.

A method for tissue decellularization that utilizes Irreversible Electroporation (IRE) and the body's immune system is disclosed. IRE is an event in which microsecond electrical pulses are applied across a cell, destabilizing the electrical potential across the cell membrane and resulting in irreversible nanoscale pores in the lipid bilayer and cell death due to loss of cell homeostasis[10,11,12]. NTIRE results when the electrical parameters are chosen such that the cell membrane is selectively targeted without inducing thermal damage to the rest of the tissue. This non-thermal method has been proven through applications such as mathematical modeling[13] and in vivo treatment of porcine atrial appendages[14]. Due to its non-thermal nature, NTIRE does not affect connective tissue nor does it denature molecules and collagen, eliminating any injuries to the cell scaffold[15]. It has also been shown that IRE does not compromise the blood vessel matrix[16], and that IRE results in a clear margination of treated and non-treated areas[14,15,17].

Recently, our group has investigated the effect of NTIRE on blood vessels for use in the treatment of restenosis[15,16,18]. Maor et. al.[18] has shown that NTIRE can ablate vascular smooth muscle cells (VSMC) within seconds without causing damage to the extra-cellular components, demonstrating a possible treatment method for restenosis.

Several methods can use NTIRE to derive a decellularized tissue scaffold, with the most straightforward being to simply apply NTIRE to the xenograph or a human donor just prior to implantation. The simplicity of this method is substantially advantageous. However, the immune process involved in the removal of the dead cells by the host organism may prove detrimental to the host. Others have carried out research on the immunological response to NTIRE cell damage[19,20].

Another method, inspired by our previous observations, may be more immediately applicable. It involves applying NTIRE to the donor tissue, waiting for the donor's own immune system to depopulate the cells, and then harvesting the remaining tissue scaffold. The decellularized construct would then be implanted into the recipient, and the cells allowed to repopulate in vivo.

To characterize the ability of NTIRE to decellularize tissue, a series of electric pulses were applied to the carotid artery in an in vivo rat model. The voltage, time and number of pulses parameters were chosen to produce IRE without resulting in thermal damage due to joule heating. At three, five, and seven days following the NTIRE-treatment, arteries were extracted for analysis.

Histological analysis of the carotid artery three, five, and seven days after being treated with NTIRE was used to compare the NTIRE-treated group (right column) and the control group (left column of FIG. 1). Compared with the control, successful NTIRE resulted in an artery that was largely decellularized three days post treatment. The structure of the decellularized artery remained intact in comparison with the control.

The images in the right column of FIG. 1 show that the endothelial layer has not yet recovered three days post-treatment. After five days, histological analysis shows that the VSMC are almost completely ablated when treated with the electric pulse. Also, new cells are evident along the endothelial layer of the NTIRE-treated artery. From the 7-day group (FIGS. 1(e) and 1(f)), it is evident that the artery remains mostly decellularized around its entire circumference when treated with NTIRE. The endothelial cells provide an even coating along the inside of the decellularized artery and are similar in number to those of the non treated control arteries.

Figure 2:
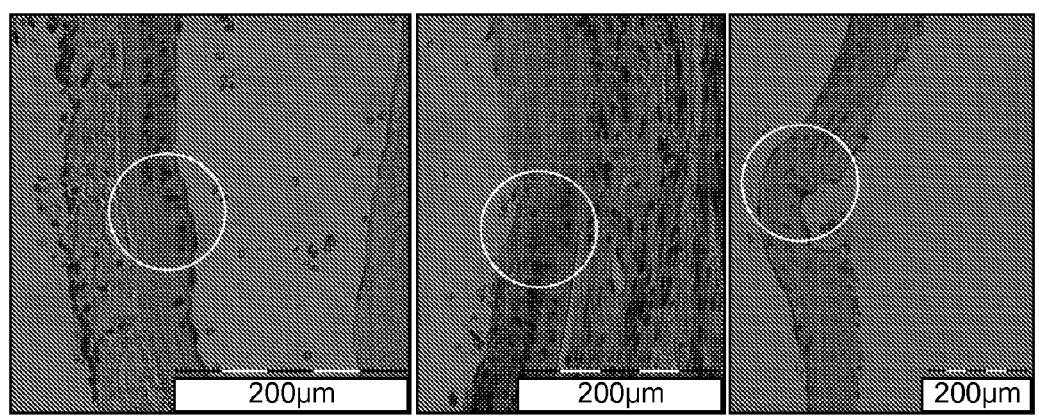
FIG. 2. Ablation zone boundary. Marked margination between VSMC-populated and depopulated regions are highlighted in three different examples.
Figure 3:
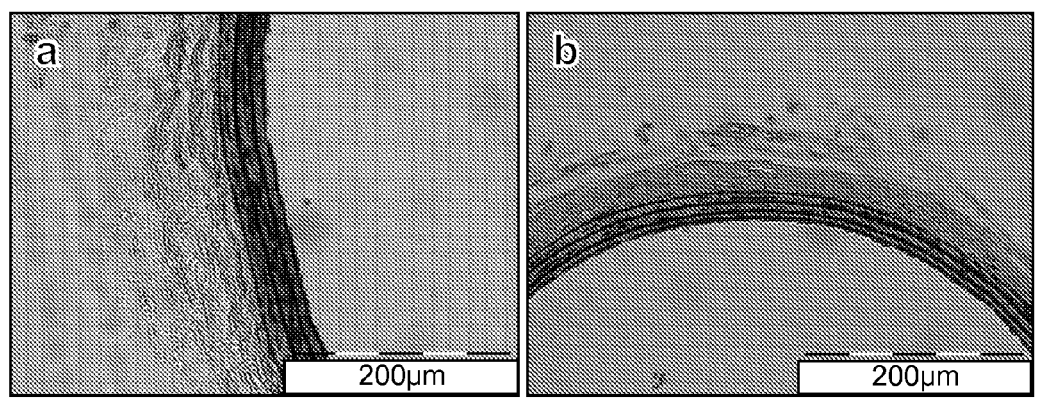
FIG. 3. EVG staining. Seven days post treatment, EVG stain shows undamaged elastic fibers for the NTIRE-treated artery (b) when compared to the control (a).

Histological analysis of both the 3-day (FIG. 1(a)) and the 5-day (FIG. 1(c)) groups revealed sections along the artery's length where the Tunica Media transformed from being completely populated by VSMC to being fully decellularized. These delineated sections are highlighted in FIG. 2.

EVG staining at seven days post treatment showed evidence of intact elastic fibers and preserved vessel wall in the NTIRE treated tissue (3(a)) as compared to the untreated tissue (3(b)).

The invention shows the use of NTIRE and the systemic immune system to derive a functional decellularized tissue scaffold. By applying irreversible electroporation to the carotid artery in vivo and controlling the electric parameters such that thermal damage is avoided, one can effectively ablate the cells within the artery wall without damage to the ECM. Over time, the body naturally clears away the dead cell debris, and there is a period of time in which the artery becomes decellularized before new cells begin to grow back.

In a second embodiment the decellularized tissue is harvested and implanted in the recipient. Thus, the method provides a decellularized artery in vivo which is be extracted from a host and put to use in a recipient animal (e.g. human) as a graft for revascularization surgeries.

The NTIRE procedure of the invention can be used to treat small intestine submucosa (SIS) with the need for chemicals, enzymes, physical or other treatment means. There are multiple patents and publications that describe in detail the characteristics and properties of small intestine submucosa (SIS). See, for example, U.S. Pat. Nos. 5,352,463, 4,902,508, 4,956, 178, 5,281,422, 5,372,821, 5,445,833, 5,516,533, 5,573,784, 5,641,518, 5,645,860, 5,668,288, 5,695,998, 5,711,969, 5,730,933, 5,733,868, 5,753,267, 5,755,791, 5,762,966, 5,788,625, 5,866,414, 5,885,619, 5,922,028, 6,056,777, and WO 97/37613, incorporated herein by reference. SIS, in various forms, is commercially available from Cook Biotech Incorporated (Bloomington, Ind.). Further, U.S. Pat. No. 4,400,833 to Kurland and PCT publication having International Publication Number WO 00/16822 provide information related to bioprosthetics and are also incorporated herein by reference.

An extracellular matrix of the invention may be attached and reinforced using bioadsorbable fabrics and sutures either of which may be synthetic non-bioabsorbable or bioabsorbable materials. Autografting, where tissue is taken from another site on the patient's body, is another means of soft tissue reconstruction. Yet another means of repair or reconstruction can be achieved through allografting, where tissue from a donor of the same species is used. Still another means of repair or reconstruction of soft tissue is through xenografting in which tissue from a donor of a different species is used.

Fiber is intended to identify a synthetic reinforcement component present within the implant to contribute enhanced mechanical and handling properties. The reinforcement component is preferably in the form of a braided suture or a mesh fabric that is biocompatible. The reinforcement component may be bioabsorbable as well.

The reinforcing component if used with the present invention may be comprised of any absorbable or non-absorbable biocompatible material, including textiles with woven, knitted, warped knitted (i.e., lace-like), non-woven, and braided structures. In an exemplary embodiment the reinforcing component has a mesh-like structure. In any of the above structures, mechanical properties of the material can be altered by changing the density or texture of the material. The fibers used to make the reinforcing component can be, for example, monofilaments, yarns, threads, braids, or bundles of fibers. These fibers can be made of any biocompatible material, including bioabsorbable materials such as polylactic acid (PLA), polyglycolic acid (PGA), polycaprolactone (PCL), polydioxanone (PDO), trimethylene carbonate (TMC), polyvinyl alcohol (PVA), and copolymers or blends thereof.

Within three to five days after NTIRE the artery may reach its peak level of decellularization. For harvesting, it is important to determine a time (1) after the ablated cells have been removed from the artery wall and (2) before the endothelial layer begins to regenerate. The 3-day and 5-day results shown here demonstrate the possibility of such an event.

Previous work in the field of tissue scaffolding has developed other potential techniques to decellularize arteries, blood vessels, and other tissues[3,6,7,8]. Most of these methods, however, require the use of chemicals and enzymes that may cause harm to the ECM, remove signaling proteins, or leave behind toxins that could reduce cell ingrowth and lead to graft failure[9]. The present invention does not strictly exclude the use of any chemicals or enzymes or other means to clean away treated material (e.g. proteins, cells, etc). However, in one embodiment of the invention the method of producing an extracellular matrix can be carried out by using NTIRE followed by the patient's own immune system removing cells which have been killed followed by no further treatment. After the patient's immune system has carried away cells which have been killed the tissue material may be removed and used as is or may be removed and washed with a mild rinse which may comprise water or a saline solution.

Signaling molecules and proteins as well as the ECM are not harmed by NTIRE in the way they are by the application of chemicals and enzymes. By its very nature IRE affects only the cell membrane's lipid bilayer, making IRE a very selective method for cell ablation. By controlling the electrical parameters, joule heating can be kept to a minimum, eliminating undesired thermal damage to the tissue as demonstrated in previous work[13,15]. Mathematical modeling (using COMSOL Multiphysics 3.5a) of the effects of the electrical parameters used in this study on the temperature of the tissue indicates that the maximum temperature experienced by the artery was approximately $39.25°$ C., keeping the tissue below the thermal damage threshold of $42°$ C.[21,22]. EVG staining of the 7-day group revealed intact collagen fibers and vessel walls for treated arteries that are similar to that of the control, further verifying that the tissue is not damaged by thermal effects when subjected to NTIRE.

After carrying out NTIRE the ECM of the decellularized tissue has remained functional. Further, the endothelial cells began to regenerate after five days and were completely regenerated after seven days. This endothelial regrowth indicates that the arteries retain their function after NTIRE-treatment and that problems such as thrombogenicity experienced by other xenographs are avoided. Another advantage of the NTIRE-derived scaffold method is its overall simplicity and relative speed. These results show that an artery can be decellularized within less than a week using a very simple and inexpensive procedure. NTIRE is also a very predictable and controllable technology. The ablation zone is well defined as depicted in the three images shown in FIG. 2, demonstrating the clear margination between treated and untreated sections of the artery. The ability to focus the NTIRE to a particular area of a targeted tissue is consistent with previous work[14,15,17] and indicates that NTIRE can be used to decellularize an artery without causing damage beyond the ablation zone to the surround tissue.

In this study, the carotid artery was exposed in order to apply the electric pulse. The procedure may, however, be performed minimally invasively, utilizing an intravascular device to induce decellularization.

The combined effects of NTIRE and the immune system will decellularize an artery for future tissue scaffold use and the artery ECM is still functional 7-day post treatment. NTIRE can be used for tissue engineering which, as a first application, is useful in any of (1) deriving a construct for use in revascularization surgeries, (2) meeting a need that autologous and synthetic grafts cannot fully reach, and (3) resulting in a successful implantation into a recipient without further complications.

DECELLULARIZED TISSUE MATRIX

Complex organs such as a heart, lung, stomach, intestine, bladder, uterus, and in particular various tubular components such as veins and arteries, esophagus, and other components of a body can be produced in accordance with the invention using the invention to produce the underlying scaffolding and then seeding that scaffolding with the appropriate cellular material. It is known that cells will grow if given the appropriate environment. Further, it is known that certain cells such as stem cells and in particular embryonic stem cells and adult stem cells have the potential to mature to virtually any type of cell and tissue provided they are placed in an appropriate environment and provided with chemical signals in order to drive their differentiation into specific cell types allowing them to form three-dimensional tissue structures. In accordance with the present invention NTIRE can be used in order to disrupt the cells and leave the basic tissue scaffolding structure in place. Thereafter, the immune system of the animal can remove the cellular materials and proteins in order to substantially reduce any immune response in a recipient. When the cellular materials have been removed the basic structure may be seeded with appropriate cells which may be embryonic or adult stem cells or may be endothelial cells in the case of vessels. Those cells used for seeding the basic scaffolding structure may be cells derived from the animal which is to receive the implant. Thus, when the scaffolding structure which has been seeded is put in place the cells which have been seeded into the structure will grow. Because the cellular material has been previously removed an immune response is eliminated or at least substantially reduced.

Others have carried out the production of decellularized matrix in the form of a heart. For example, see Harald C. Ott et al., "Perfusion-decellularized matrix: using nature's platform to engineer a bioartificial heart," Nature Medicine, 14:213-221 (2008).

Although Ott et al. demonstrate the proof of principle Ott et al. do not use NTIRE.

EXAMPLE

The following example is put forth so as to provide those of ordinary skill in the art with a complete disclosure and description of how to make and use the present invention, and are not intended to limit the scope of what the inventors regard as their invention nor is it intended to represent that the experiment below is the only experiment performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Methods

The experimental protocol used here follows that used by Maor et. al. to ablate blood vessel cells with NTIRE for the treatment of restenosis[18]. Nine Sprague-Dawley rats weighing 200-300 grams were used in this study. All animals received humane care from properly trained professionals in compliance with both the Principals of Laboratory Animal Care and the Guide for the Care and Use of Laboratory Animals, published by the National Institute of Health (NIH publication No. 85-23, revised 1985).

Animals were anesthetized with an intramuscular injection of Ketamin and Xylazine (90 mg/kg and 10 mg/kg, respectively), and anesthesia was administered throughout the procedure with vaporized isoflurane. The left common carotid artery of each animal was exposed and a custom-made electrode clamp, as described previously[15], was applied very close to the carotid artery's bifurcation. The measured distance between the electrodes was approximately 0.4 mm. A sequence of 90 dc pulses of 70 V (corresponding to an electric field of approximately 1,750 V/cm), 100 µs each, and a frequency of 1 Hz was applied between the electrodes using a high voltage pulse generator designed for electroporation procedures (ECM 80, Harvard Apparatus, Holliston, Mass.). These parameters were chosen due to their ability to produce irreversible electroporation without causing thermal damage, as shown in previous work[18] and by computer modeling. The procedure was repeated in two successive locations along the common carotid artery, treating approximately 1.5 cm along the length. The right common carotid artery was left alone and used as a control. The animals were divided into two groups. The first group, consisting of five animals, was kept alive for three days, whereas the second group, consisting of four animals, was kept alive for a 5-day follow-up period prior to being euthanized. In a second series of NTIRE-treatments, a frequency of 4 Hz was applied for a more rapid procedure, utilizing essentially the same electrical parameters (90 pulses, 1,750 V/cm, 100 µs pulse interval) as seen for the 3-day and 5-day groups. This last group was given a 7-day follow-up period.

Animals were euthanized by bilateral chest dissection while under a deep anesthesia induced by an overdose of Xylazine and Ketamin. The arterial tree was perfused with 10% buffered formalin and the left and right carotid arteries were harvested near the bifurcation of the internal and external carotid arteries. Each artery was fixed with 10% buffered formalin, embedded in paraffin, and sectioned with a microtome (5-µm-thick). Three samples from the 3-day group and four samples from the 5-day group were cut longitudinally along the length of the artery, and two samples from the 3-day group were cut perpendicular to the axis, exposing the artery's cross-section. Each section was stained with hematoxylin and eosin. The 7-day samples were cut in cross-section, and some of the sections were stained with hematoxlin and eosin, while selected sections were stained with elastic Van Gieson (EVG) and Masson trichrome in order to examine the integrity of the extra-cellular elastic and collage fibers.

Examination of each section for three, five, and seven days was focused on the effect of NTIRE on the cells in the Tunica Media as well as the endothelial layer. The structure of the ECM for treated arteries was compared to that of non-treated arteries to ensure that the ECM was not damaged by the applied electric pulse.

REFERENCES

1.) Badylak, S. The extracellular matrix as a biologic scaffold material. *Biomaterials*. 28 3587-3593 (2007).
2.) Campbell, G., Campbell, J. Development of tissue engineered vascular grafts. *Curr. Pharm. Biotechnol.* 8, 43-50 (2007).
3.) Huynh, T., et al. Remodeling of an acellular collage graft into a physiologically responsive neovessel. *Nat. Biotechnol.* 17, 1083-1087 (1999).
4.) Conklin, B., Richter, R., Kreutziger, K., Zhong, D., Chen, C. Development and evaluation of a novel decellularized vascular xenograft. *Med. Eng. Phys.* 24, 173-183 (2002).
5.) Yow, K., Ingram, J., Korossis, S., Ingham, E., Homer-Vanniasinkam, S. Tissue engineering of vascular conduits. *Br. J. Surg.* 93, 652-661 (2006).
6.) Clarke, D., Lust, R., Sun, Y., Black, K., Ollerenshaw, J. Transformation of nonvascular acellular tissue matrices into durable vascular conduits. *Ann. Thorac. Surg.* 71, S433-S436 (2001).
7.) Conconi, M., et al. Tracheal matrices, obtained by a detergent-enzymatic method, support in vivo the adhesion of chondrocytes and tracheal epithelial cells. *Transpl. Int.* 18, 727-734 (2006).
8.) Flynn, L., Semple, J., Woodhouse, K. Decellularized placental matrices for adipose tissue engineering. *J. Biomed. Mater. Res. A.* 79(2), 359-369 (2006).
9.) Gilbert, T., Sellaro, T., Badylak, S. Decellularization of tissues and organs. *Biomaterials* 27, 3675-3683 (2006).
10.) Weaver, J. Electroporation of biological membranes from multicellular to nano scales. *IEEE T Dielect. El. In.* 10(5), 754-768 (2003).
11.) Lee, R. Cell injury by electric forces. *Ann. N.Y. Acad. Sci.* 1066, 85-91 (2005).
12.) Lee, R., Kolodney, M. Electrical injury mechanisms: electrical breakdown of cell membranes. *Plast. Reconstr. Surg.* 80(5), 672-679 (1987).
13.) Davalos, R., Mir, L., Rubinsky, B. Tissue ablation with irreversible electroporation. *Ann. Biomed. Eng.* 33(2), 223-231 (2005).
14.) Lavee, J., Onik, G., Mikus, P., Rubinsky, B. A novel nonthermal energy source for surgical epicardial atrial ablation: irreversible electroporation. *Heart Surg. Forum* 10(2), 96-101 (2007).
15.) Maor, E., Ivorra, A., Leor, J., Rubinsky, B. Irreversible electroporation attenuates neointimal formation after angioplasty. *IEEE Trans. Biomed. Eng.* 55(9), 2268-2274 (2008).
16.) Maor, E., Ivorra, A., Leor, J., Rubinsky, B. The effect of irreversible electroporation on blood vessels. *Technol. Cancer Res. Treat.* 6(4), 1-6 (2007).
17.) Rubinsky, B. Irreversible electroporation in medicine. *Technol. Cancer Res. Treat.* 6(4), 255-259 (2007).
18.) Maor, E., Ivorra, A., Rubinsky, B. Non thermal irreversible electroporation: novel technology for vascular smooth muscle cells ablation. *PLoS ONE* 4(3), e4757 (2009).
19.) Rubinsky, B., Onik G., Mikus, P. Irreversible Electroporation: A New Ablation Modality—Clinical Implications. Technol. Cancer Res. Treat. 6(1), 37-48 (2007).
20.) Al-Sakere, B., et al. Tumor Ablation with Irreversible Electroporation. PLoS ONE 2(11), e1135 (2007).
21.) Tropea, B., Lee, R. Thermal injury kinetics in electrical trauma. *J. Biomech. Eng.* 114, 241-250 (1992).

22.) Dickson, J., Calderwood, S. Temperature range and selective sensitivity of tumors to hyperthermia: a critical review. *Ann. N.Y. Acad. Sci.* 335, 180-205 (1980).

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A method of treatment, comprising:
    subjecting a target area of tissue in a human to non-thermal irreversible electroporation (NTIRE) to kill cells in the target area;
    allowing the human's immune system to remove cells killed with the NTIRE to provide an extracellular matrix;
    transplanting the extracellular matrix to a repair site in the human; and
    seeding the extracellular matrix with live cells obtained from the human where the repair site is located and the repair site is in the human and the live cells are human stem cells;
    wherein the method is carried out absent any immunosuppressive drug;
    wherein the tissue is tissue of an organ selected from the group consisting of a blood vessel, a heart, a lung, an intestine, and a bladder.

* * * * *

UNITED STATES PATENT AND TRADEMARK OFFICE
CERTIFICATE OF CORRECTION

| | | |
|---|---|---|
| PATENT NO. | : 8,835,166 B2 | Page 1 of 1 |
| APPLICATION NO. | : 13/391577 | |
| DATED | : September 16, 2014 | |
| INVENTOR(S) | : Mary Phillips et al. | |

It is certified that error appears in the above-identified patent and that said Letters Patent is hereby corrected as shown below:

In the specification

Please insert the following paragraph on column 1, line 4, beneath the title.

--GOVERNMENT RIGHTS
This invention was made with Government support under contract RR018961 awarded by The National Institutes of Health. The Government has certain rights in the invention.--

Signed and Sealed this
Third Day of May, 2016

Michelle K. Lee
*Director of the United States Patent and Trademark Office*